(12) United States Patent
Kietzmann et al.

(10) Patent No.: US 9,999,730 B2
(45) Date of Patent: Jun. 19, 2018

(54) COMPONENT OF A DRUG DELIVERY DEVICE AND METHOD OF ASSEMBLY

(71) Applicant: SANOFI-AVENTIS DEUTSCHLAND GMBH, Frankfurt am Main (DE)

(72) Inventors: Hardy Kietzmann, Frankfurt am Main (DE); Jasmin Groeschke, Frankfurt am Main (DE); Jan-Peter Spengler, Frankfurt am Main (DE); Matthias Scharf, Frankfurt am Main (DE); Christoph Dette, Frankfurt am Main (DE); Hanno Juhnke, Frankfurt am Main (DE); Michael Schrack, Pliezhausen (DE); Olaf Zeckai, Weinheim (DE)

(73) Assignee: Sanofi-Aventis Deutschland GmbH, Frankfur am Main (DE)

( * ) Notice: Subject to any disclaimer, the term of this patent is extended or adjusted under 35 U.S.C. 154(b) by 454 days.

(21) Appl. No.: 14/353,520

(22) PCT Filed: Oct. 29, 2012

(86) PCT No.: PCT/EP2012/071333
§ 371 (c)(1),
(2) Date: Apr. 23, 2014

(87) PCT Pub. No.: WO2013/060884
PCT Pub. Date: May 2, 2013

(65) Prior Publication Data
US 2014/0297018 A1  Oct. 2, 2014

(30) Foreign Application Priority Data
Oct. 27, 2011  (EP) ..................... 11186879

(51) Int. Cl.
*G06F 19/00* (2018.01)
*A61M 5/24* (2006.01)
(Continued)

(52) U.S. Cl.
CPC .......... *A61M 5/24* (2013.01); *A61M 5/31511* (2013.01); *G05B 19/4189* (2013.01);
(Continued)

(58) Field of Classification Search
CPC ........ A61M 5/02; A61M 5/1409; A61M 5/20; A61M 5/008; A61M 5/1454;
(Continued)

(56) References Cited

U.S. PATENT DOCUMENTS

| 533,575 A | 2/1895 | Wilkens | |
| 3,917,045 A * | 11/1975 | Williams | .............. A61J 7/0481 |
| | | | 194/210 |

(Continued)

FOREIGN PATENT DOCUMENTS

| EP | 0937471 | 8/1999 |
| EP | 0937476 | 8/1999 |

(Continued)

OTHER PUBLICATIONS

International Search Report for Int. App. No. PCT/EP2012/071333, completed Jan. 17, 2013.

*Primary Examiner* — Tuan Vu
(74) *Attorney, Agent, or Firm* — McCarter & English, LLP

(57) ABSTRACT

The present invention relates to an assembly line to assemble a medical device and comprising at least one communication member adapted to communicate with a corresponding communication member of an initial component of the device, wherein the assembly line comprises at least one assembly stage adapted to conduct at least one step (Continued)

of assembly being at least influenced by device-related data obtained from the component.

12 Claims, 3 Drawing Sheets

(51) Int. Cl.
    *A61M 5/315*      (2006.01)
    *G05B 19/418*      (2006.01)

(52) U.S. Cl.
    CPC ..... *A61M 5/31528* (2013.01); *A61M 2205/50* (2013.01); *A61M 2205/60* (2013.01)

(58) Field of Classification Search
    CPC ............... A61M 5/31511; A61M 5/24; A61M 2205/50; A61J 7/53; A61J 7/84; A61J 7/481; A61J 1/20; G07F 17/0092; A61F 2/042; B29C 45/768; A61N 1/08; A61N 1/375
    See application file for complete search history.

(56) References Cited

U.S. PATENT DOCUMENTS

| | | | |
|---|---|---|---|
| 5,208,762 A * | 5/1993 | Charhut | A61J 7/0084 |
| | | | 221/9 |
| 5,226,895 A | 7/1993 | Harris | |
| 5,259,748 A * | 11/1993 | Neko | B29C 45/768 |
| | | | 264/40.3 |
| 5,279,586 A | 1/1994 | Balkwill | |
| 5,304,152 A | 4/1994 | Sams | |
| 5,320,609 A | 6/1994 | Haber et al. | |
| 5,383,865 A | 1/1995 | Michel | |
| 5,411,480 A * | 5/1995 | Kriesel | A61M 5/1409 |
| | | | 128/DIG. 12 |
| 5,480,387 A | 1/1996 | Gabriel et al. | |
| 5,505,704 A | 4/1996 | Pawelka et al. | |
| 5,582,598 A | 12/1996 | Chanoch | |
| 5,626,566 A | 5/1997 | Petersen et al. | |
| 5,674,204 A | 10/1997 | Chanoch | |
| 5,688,251 A | 11/1997 | Chanoch | |
| 5,812,410 A * | 9/1998 | Lion | G07F 17/0092 |
| | | | 221/9 |
| 5,921,966 A | 7/1999 | Bendek et al. | |
| 5,961,495 A | 10/1999 | Walters et al. | |
| 6,004,297 A | 12/1999 | Steenfeldt-Jensen et al. | |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,899,698 B2 | 5/2005 | Sams | |
| 6,936,032 B1 | 8/2005 | Bush, Jr. et al. | |
| 7,241,278 B2 | 7/2007 | Moller | |
| 2002/0052578 A1 | 5/2002 | Moller | |
| 2002/0103505 A1 * | 8/2002 | Thompson | A61N 1/08 |
| | | | 607/1 |
| 2002/0120235 A1 | 8/2002 | Enggaard | |
| 2003/0050609 A1 | 3/2003 | Sams | |
| 2004/0059299 A1 | 3/2004 | Moller | |
| 2004/0210199 A1 | 10/2004 | Atterbury et al. | |
| 2004/0267207 A1 | 12/2004 | Veasey et al. | |
| 2005/0113765 A1 | 5/2005 | Veasey et al. | |
| 2005/0263615 A1 * | 12/2005 | Kriesel | A61M 5/1454 |
| | | | 239/373 |
| 2006/0153693 A1 | 7/2006 | Fiechter et al. | |
| 2006/0223462 A1 | 10/2006 | Rahman et al. | |
| 2007/0233001 A1 * | 10/2007 | Burroughs | A61M 5/008 |
| | | | 604/131 |
| 2009/0030366 A1 * | 1/2009 | Hochman | A61M 5/20 |
| | | | 604/67 |
| 2009/0157219 A1 | 6/2009 | Parker, Jr. et al. | |
| 2009/0275916 A1 | 11/2009 | Harms et al. | |
| 2010/0198392 A1 * | 8/2010 | Eliuk | A61J 1/20 |
| | | | 700/216 |
| 2011/0230923 A1 * | 9/2011 | Swanson | A61N 1/375 |
| | | | 607/5 |
| 2012/0022460 A1 * | 1/2012 | Horvath | A61M 5/002 |
| | | | 604/192 |
| 2012/0241043 A1 * | 9/2012 | Perazzo | A61J 7/0053 |
| | | | 141/2 |

FOREIGN PATENT DOCUMENTS

| | | |
|---|---|---|
| JP | S57-211437 A | 12/1982 |
| JP | H02-198749 A | 8/1990 |
| JP | 2000-056810 A | 2/2000 |
| JP | 2006-135946 A | 5/2006 |
| JP | 2008-538869 A | 11/2008 |
| JP | 2009-525831 A | 7/2009 |
| WO | 99/38554 | 8/1999 |
| WO | 01/10484 | 2/2001 |
| WO | 2006/107841 A2 | 10/2006 |
| WO | 2006/108026 | 10/2006 |
| WO | 2007/092637 A2 | 8/2007 |
| WO | 2010/133676 | 11/2010 |
| WO | 2011/032956 | 3/2011 |

\* cited by examiner

COMPONENT OF A DRUG DELIVERY DEVICE AND METHOD OF ASSEMBLY

CROSS REFERENCE TO RELATED APPLICATIONS

The present application is a U.S. National Phase Application pursuant to 35 U.S.C. § 371 of International Application No. PCT/EP2012/071333 filed Oct. 29, 2012, which claims priority to European Patent Application No. 11186879.0 filed Oct. 27, 2011. The entire disclosure contents of these applications are herewith incorporated by reference into the present application.

TECHNICAL FIELD

The present invention relates to the field of drug delivery devices as well as to cartridges containing a medicament to be dispensed by such devices. The invention also relates to a method of assembling a drug delivery device by making use of data stored in and provided by the cartridge or some other device component.

BACKGROUND

Drug delivery devices for setting and dispensing a single or multiple doses of a liquid medicament are as such well-known in the art. Generally, such devices have substantially a similar purpose as that of an ordinary syringe.

Drug delivery devices, in particular pen-type injectors have to meet a number of user-specific requirements. For instance, with patient's suffering chronic diseases, such like diabetes, the patient may be physically infirm and may also have impaired vision. Suitable drug delivery devices especially intended for home medication therefore need to be robust in construction and should be easy to use. Furthermore, manipulation and general handling of the device and its components should be intelligible and easy understandable. Moreover, a dose setting as well as a dose dispensing procedure must be easy to operate and has to be unambiguous.

For instance, such devices comprise a housing to receive a cartridge being at least partially filled with the medicament to be dispensed. The device further comprises a drive mechanism, typically having a displaceable piston rod to operably engage with a piston of the cartridge. By means of the drive mechanism and its piston rod, the piston of the cartridge can be displaced in a distal or dispensing direction and may therefore expel a pre-defined amount of the medicament via a piercing assembly which is to be releasably coupled with a distal or dispensing end of the housing of the drug delivery device.

Drug delivery devices, such as pen-type injectors are commonly manufactured in large quantities by way of an assembly line in a mass production environment. Especially with pen-type injectors but also with other drug delivery devices, the primary packaging containing and providing the medicament can be readily provided with a dispensing mechanism. The device may be designed as a disposable device, which after use or consumption of the medicament is to be discarded. For safety reasons, charges or batches of drug delivery devices, especially those having a medicament containing cartridge readily disposed therein, have to be unequivocally retraceable even after the drug delivery device and the medicament therein have been distributed across various trade channels.

Retraceability of medicaments and/or drug delivery devices associated therewith imposes a respective burden on the manufacturer. If for instance a medicament or a device belonging to a particular charge exhibits a malfunction or some other kind of defect, all further entities of the respective charge should not enter the market or have to be fetched back.

There exist various approaches to individually assign single entities of primary packagings of liquid medicaments. For instance, WO 20011/032956 A2 discloses a stopper for sealing a compartment of a medicament container, wherein a microchip comprising at least one sensor is embedded into said stopper. The microchip is arranged for storing data comprising measurement data acquired by the sensor and the microchip further comprises wireless communication means for allowing the stored data to be retrieved by an external wireless unit. This for instance allows to provide the medicament container with an ID upon manufacturing in order to make it tamper-proof. Moreover, data may be stored into the microchip upon production via the wireless communication. The data may comprise time stamps for each manufacturing step in order to be able to retrace the production chain and/or the whole life cycle of the cartridge.

Individual labelling of single units of medicament containers or drug delivery devices requires to handle such data appropriately. Since hundreds of thousands or even millions of medicament containers are for instance to be produced in only a months time, a tremendous amount of data will be generated that has to be appropriately handled and stored over a comparatively long time interval. Moreover, by treating and handling any device component individually, a rather sophisticated and complicated logistic concept is required in general.

It is therefore one object of the present invention to provide a new concept of manufacturing medical devices, especially drug delivery devices equipped with a medicament containing cartridge, wherein product related data can be used in a more efficient way. Moreover, it is a further object, to provide improved control and release mechanisms in an assembly line for assembling drug delivery devices. Additionally, a new and beneficial logistic concept is to be achieved making use of individually labelling selected device components by simultaneously reducing the amount of data to be stored and handled by the device manufacturer.

SUMMARY

In a first aspect, a device component of a medical device is provided, wherein the device is preferably adapted to dispense a medicament. The component may for instance comprise a cartridge having a container or a barrel to receive and/or to store the medicament. Such container or barrel is typically sealed by way of a piston slidably disposed therein. Hence, the cartridge may comprise a carpule, ampoule or a syringe, wherein by application of mechanical pressure to a piston, a liquid medicament can be expelled via a distal outlet. In case of a carpule, the distal end of the container is sealed by means of a flexible septum pierceable by a piercing element, like a double-tipped needle, to provide injection of the medicament into biological tissue.

The device component comprises a microprocessor and at least one communication member, preferably a wireless communication member to provide device-related data to an automated assembly line which is adapted to assemble the device or components thereof. This way, the component which may comprise or serve as a primary packaging is provided with medical device-related data by way of which the process of assembly of e.g. a drug delivery device can be at least modified according to the type of data stored in the component.

In the following, the device component being equipped with the communication member and the microprocessor is denoted as initial device component from which a process of assembly may start. Identifying the particularly adapted device component as initial component does not necessarily require that the assembly process has to start with this particular component. Hence, a respective method of assembly may equally start with a pre-assembly of the medical device wherein several components of the device are pre-configured or pre-assembled when getting subject to the assembly process according to the present invention.

The communication member and/or the microprocessor may for instance be embedded or disposed in a piston of the cartridge serving as an initial device component. The communication member is for instance based on RFID communication technology and may provide stored data on request. Consequently, the entire process of manufacturing a drug delivery device can be triggered, controlled and/or governed by a cartridge or some other suitable device component to be assembled in the device. The component itself may therefore be used to provide individual and device specific information to various assembly stages of the assembly line. Device specific data management during assembly of such drug delivery devices as well as the logistic concept regarding planning of drug delivery device assembly can be simplified.

The communication member may be provided as a separate unit being in electrical contact with the microprocessor or it may be integrated therein. Hence, microprocessor and communication member may be integrated in a common microchip.

In a preferred embodiment, the component further comprises a writable storage to store assembly-related information during the various steps of assembly. Hence, the communication member is not only adapted to provide information to the assembly line but is also operable to receive information from the assembly line and to store respective assembly-related data. This way, data regarding various subsequent steps of production or assembly can be individually stored in each device component which is suitable for data storage. This way, the entire production or assembly chain of a medical device, in particular of a drug delivery device, the component is assembled in can be appropriately stored in the component itself.

Moreover, by providing a writable storage, it is also possible to interlink or to coordinate various subsequent steps of assembly via the device component. For instance, in a first assembly step, respective first assembly-related data may be stored in the storage. Then, in a subsequent second step of assembly, said first data may be retrieved and processed in order to modify or to manipulate the second step of assembly.

The storage may be separately embedded in or on the component or may also be integrated in the microchip.

In a further preferred embodiment, the storage of the component comprises a complete or partial assembly configuration of the drug delivery device. Furthermore, the microchip and/or its microprocessor together with the communication member is operable to instruct the assembly line, or at least one assembly stage thereof regarding actual and/or proceeding steps of assembly according to the data stored in the storage.

By simply programming or pre-configuring a device component, e.g. a cartridge, with device-related data, the entire production- or assembly line may be appropriately instructed which component of a drug delivery device has to be taken and in which way it is to be assembled. This way, a large variety of differently configured medical devices of similar or different type can be assembled by a single production line. Device-related converting of the production line and/or of various assembly stages thereof is generally no longer required.

If for instance a large variety of differently configured device components is generally available, it is the selected device component which governs and determines which type of a component of the drug delivery device is to be combined and to be assembled with the present configuration of an actual component and/or with a respective pre-assembly of the device. In this context a pre-assembly of the device is attained when the initial or selected component has passed a first or subsequent steps of assembly, and is therefore already assembled with at least one additional component.

According to a further preferred aspect, the microchip of the initial component is adapted or operable to select and/or to determine the type and/or the configuration of a component of the drug delivery device to be subsequently assembled either directly therewith or with the available pre-assembly. An assembly stage, the initial component, e.g. a cartridge or a respective pre-assembly of the drug delivery device is exposed to, then automatically determines and controls the assembly step to be conducted by the respective assembly stage.

According to another preferred embodiment, the microchip is also adapted to process the assembly-related data and/or to process drug delivery device-related data, e.g. in order to determine, whether pre-defined conditions of assembly are met. Hence, the initial component or a respective pre-assembly is adapted to determine itself, whether it is actually subject to a correct and appropriate assembly. In case that the microprocessor determines that the initial component or the pre-assembly is or was handled inappropriately, a respective indicator flag can be set and the respective cartridge or pre-assembly can be electronically labelled as being erroneous.

Accordingly and following another preferred aspect, the microprocessor may be also adapted to validate and/or to approve if the drug delivery device or the pre-assembly fulfils pre-defined conditions of release. Such a release or quality check may be executed and conducted prior, during and/at or after each or at least one selected stage of assembly. This way, any inappropriate assembly of the drug delivery device can be detected as soon as it occurs, thereby allowing to eject the respective pre-assembly from the further processing of the device assembly. As a consequence, production and manufacturing capacities can be optimized and cartridges featuring detectable effects or malfunctions will not further become subject to device assembly.

In effect and according to a further preferred embodiment, it is the microprocessor itself which in response of determining that at least one pre-defined condition of release is not met is operable to request to get ejected from the assembly line. This way, quality control of the manufacturing and/or assembly process can be enhanced. Separate or conventional, rather complex quality surveying means do no longer have to be implemented, especially at the end of a manufacturing or assembly process.

In a further independent aspect, the invention also relates to an assembly line to assemble a drug delivery device. The assembly line comprises at least one communication member adapted to communicate with a corresponding communication member of an initial device component as described above and which is to be assembled in the medical device, preferably in a drug delivery device. The assembly line further comprises at least one assembly stage being adapted or operable to execute or to conduct at least one step of assembly, wherein the step of assembly is at least influenced by device-related data obtained or read-out from the communication member of the drug delivery device.

Medical device-related data may be specific about the sequence and types of components which have to be mutually assembled according to a pre-defined schedule or configuration. This way, the process of assembly may be at least influenced or partially controlled by device-related data stored in and provided by the initial device component.

In a further preferred embodiment, the assembly stage is particularly adapted to select at least one component of the drug delivery device among a plurality of generally available components. Furthermore the assembly stage is adapted to assemble the selected component with the initial component or with a pre-assembly on request of the cartridge's microprocessor.

In a further preferred aspect, the at least one assembly stage is also adapted to store assembly-related data or parameters in the storage of the initial component. This way, the component itself may be provided with assembly-related data, thereby providing storage of an entire product- or assembly chain of the medical device in the device itself.

According to another preferred embodiment, it is also conceivable, that the assembly line comprises a release stage to read-out the storage of the initial component and to determine whether pre-defined conditions of release are met. Hence, the release stage may serve as a kind of quality check, wherein assembly specific data stored in the storage can be read-out and appropriately processed. If for instance any pre-defined condition of release is not met, the release stage may sort out the corresponding device or a respective pre-assembly.

Additionally or alternatively, the release stage may be further adapted to process an ejection command transmitted by the drug delivery device or by a respective pre-assembly. Then, in response of receiving a request of ejection, the release stage may take away the respective drug delivery or pre-assembly from the assembly line.

In still another aspect, the invention also relates to a method of assembling a drug delivery device comprising the steps of providing an initial device component, e.g. a cartridge as described above, and receiving device-related data therefrom. Thereafter, a specific device component is selected according to the received data. The selected device component is then assembled to the initial component, thereby forming a pre-assembly of the drug delivery device.

In a preferred embodiment during, prior or after the step of assembly, assembly-related data can be stored in the storage of the initial component and the pre-assembly can be passed over to a proceeding step or stage of assembly, where further device components can be assembled or configured in a similar manner with said pre-assembly, e.g. until the drug delivery device is completed.

In a preferred embodiment, the complete assembly configuration of the drug delivery device is stored in the initial component. The initial component itself may therefore comprise all instructions necessary to assemble and/or to configure the drug delivery device. Furthermore, the initial component, e.g. a cartridge may actively instruct, configure or trigger actual or subsequent stages and steps of assembly according to pre-defined data or by way of the data previously stored during the assembly process.

It is to be noted here, that the method is by no way limited to the assembly or production of cartridges and drug delivery devices such as pen-type injectors. In general, the described concept of assembly may be accordingly transferred to various different types of assembly processes for medical devices in general.

An assembly of a medical device and/or of a drug delivery device may start from a medicament-containing entity, like a cartridge and may end with providing the drug delivery device in a secondary packaging, e.g. together with language-specific leaflets, patient- and/or price information. The present invention in general provides individual labelling of single drug delivery devices, wherein also all quality-relevant data can be provided directly on the respective device.

Product release can be conducted on the basis of single or individual devices, thereby making an overall control of the entire production process substantially superfluous. Line clearance, converting of assembly or manufacturing stages, documentation of charges does in principle no longer have to be provided.

In effect, the present invention provides a total monitoring and control of the assembly and production during every single process or assembly step on the basis of the individual devices themselves. This way, a multiplicity of quality checks can be conducted, even after every single step of manufacturing or assembly.

In another aspect, it is also possible to widen tolerance regimes of selected components or parts a medical device, especially a drug delivery device is made of. When various components are precisely characterized, in particular in terms of their geometric size, only those components may be selected that match with regard to their geometric tolerances. Alternatively, it is conceivable, that only tolerance-specific information about any single component is stored in the device-specific storage.

Then, at the end of the assembly or manufacturing process, the release stage may read-out and process respective geometric tolerance information in order to identify, whether the combination of device components mutually assembled still fall within a pre-defined tolerance regime. In such cases, wherein pre-defined tolerance requirements are not met, a respective device or pre-assembly can be individually identified, traced and/or taken away from the further process of manufacturing or assembling.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36[Asp28] Exendin-4(1-39),
des Pro36[IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36[Trp(O2)25, Asp28] Exendin-4(1-39),
des Pro36[Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group-Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
h-(Lys)6-des Pro36, Pro37, Pro38[Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38[Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36[Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystallizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the pertinent art that various modifications and variations can be made to the present invention without departing from the spirit and scope of the invention. Further, it is to be noted, that any reference signs used in the appended claims are not to be construed as limiting the scope of the present invention. Moreover, all features and embodiments as described herein are to be understood to equally apply to the initial device component, to the medical device including such component, to the assembly line as well as to the method of assembly. In particular, a mentioning of a component or an assembly stage being configured or arranged to conduct a particular operation is also to be understood to disclose a respective method step and vice versa.

BRIEF DESCRIPTION OF THE DRAWINGS

In the following preferred embodiments of the invention will be described in detail by making reference to the drawings, in which.

DETAILED DESCRIPTION

Figure 1:
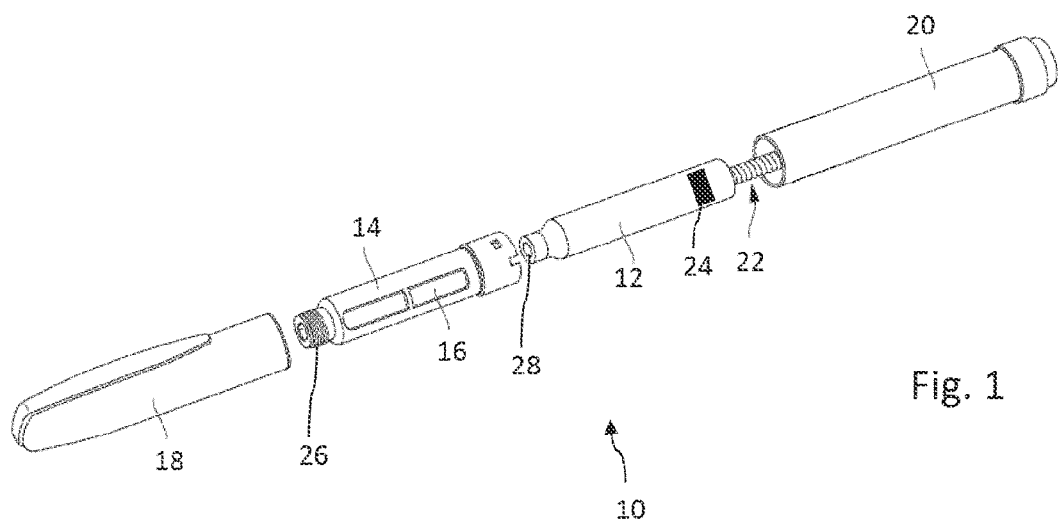
FIG. 1 shows an exploded and perspective view of a drug delivery device in form of a pen-type injector.

The drug delivery device 10 as illustrated in FIG. 1 is configured as a pen-type injector. The device 10 comprises a proximal housing component 20 to be interconnected with a distal housing component 14 that serves as a cartridge holder. Inside the device 10, a cartridge 12 at least partially filled with a medicament to be dispensed by the device 10 is disposed in the cartridge holder 14. Said cartridge holder 14 further comprises an inspection window 16 by way of which a filling level of the cartridge 12 can be visually inspected.

The cartridge holder 14 further comprises a threaded socket 26 near a distal end thereof which serves as a mount for a correspondingly threaded needle hub. By screwing a needle hub onto the threaded socket 26, e.g. a double-tipped injection needle may penetrate a distal seal 28 of the cartridge 12 to gain access to the medicament provided therein.

The cartridge 12 further comprises a piston 24 near its proximal end which is typically slidably disposed in the e.g. tubular-shaped vitreous body of the cartridge 12. The piston 24 is to be displaced in distal direction, hence towards the seal 28 by way of a piston rod 22 of a drive mechanism of the drug delivery device 10. The drive mechanism, which is not further illustrated here, at least comprises the piston rod 22 as well as various control components, such like a dose dial or a dose button. The drive mechanism and its mechanical components is housed and assembled in the proximal housing 20.

During assembly of the drug delivery device 10, a pre-filled cartridge 12 is to be assembled in the cartridge holder 14, thereby forming a cartridge holder pre-assembly. In a similar way, also the drive mechanism and/or the piston rod 22 can be separately assembled in the housing 20 to form a housing pre-assembly. In a final step of assembly, cartridge holder 14 and housing 20 pre-assemblies can be interconnected, e.g. by making use of positively engaging interlock members and/or by making use of adhesives or other bonding means, such like laser or ultrasonic welding. Finally, a protective cap 18 is to be releasably disposed over the cartridge holder 14.

Figure 2:
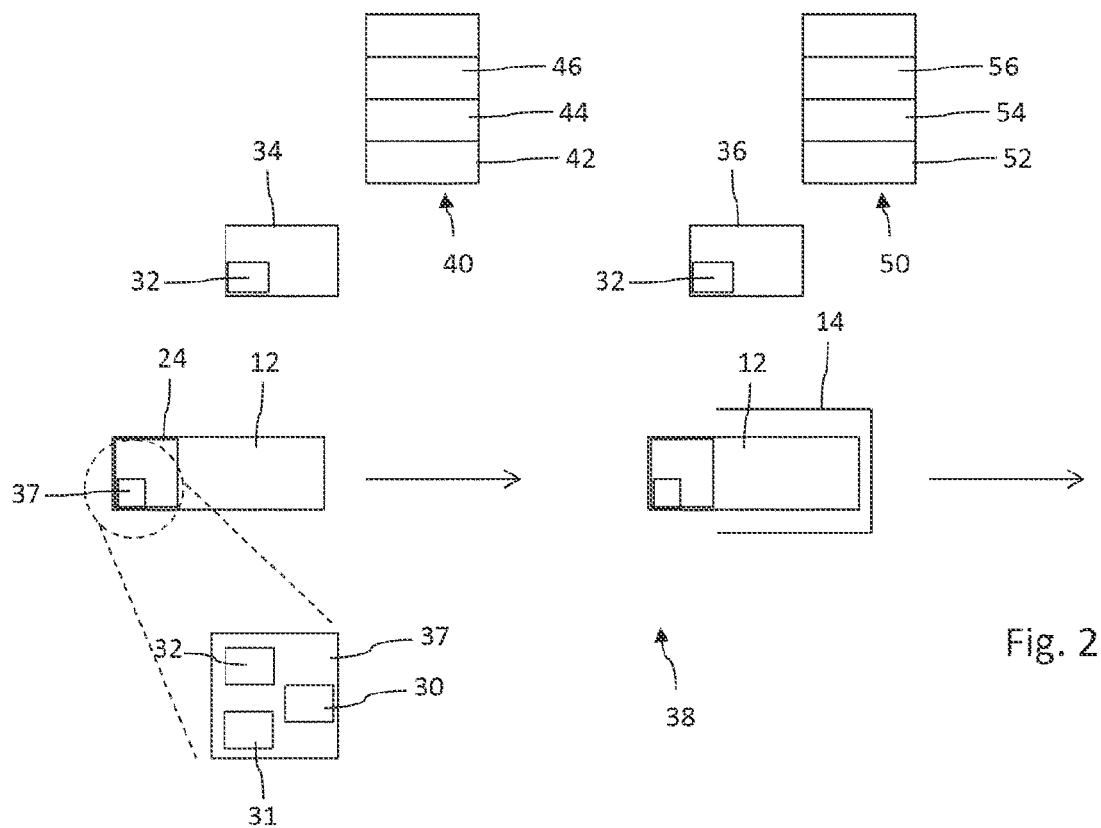
FIG. 2 is indicative of an assembly line to assemble a device according to FIG. 1.

An assembly line adapted to assemble or to manufacture a drug delivery device 10 as shown in FIG. 1 is illustrated in FIG. 2. The assembly line 38 comprises at least two assembly stages 34, 36 each of which having an own communication member 32 in order to wirelessly communicate with at least one initial component of the drug delivery device. Preferably but not exclusively, the cartridge 12 may serve as an initial component and may be provided with a microprocessor 30 having a communication member 32 in order to communicate with the respective communication members 32 of the assembly line 38.

The microprocessor 30 is preferably embedded in the piston 24 of the cartridge 12. The microprocessor 30 may interact with the communication member 32 as well as with a storage 31 in order to store medicament- and/or drug delivery device-specific data. Preferably, microprocessor 30, storage 31 and communication member 32 are integrated and/or embedded in a single microchip 37.

Figure 3:
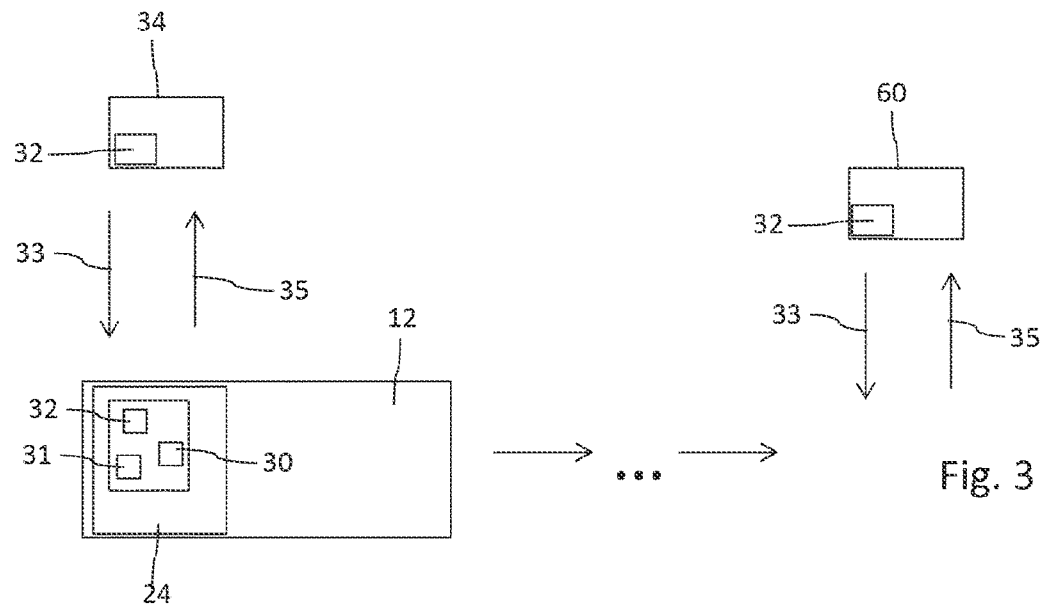
FIG. 3 is further indicative of the wireless communication between a cartridge and various stages of assembly.

In an initial step of assembly as illustrated in FIG. 3, the cartridge 12, in particular its microchip 37 sends a request 35 to the communication member 32 of an assembly stage 34 being in close vicinity and being adapted to appropriately communicate with the microchip 37. The assembly stage 34 may confirm the request 35 and may start to process the data transmitted via the request 35.

The request 35 may comprise information such that the cartridge 12 comprises a particular medicament having a particular identification code and featuring a respective best-before date. Moreover, the request 35 may comprise data regarding geometric properties of the cartridge 12. Additionally, the request 35 may comprise drug delivery device-specific data. Hence, the storage 31 of the cartridge 12 may comprise data, which types of components 12, 14, 18, 20, 22 of the drug delivery device 10 may be used for a particular configuration of the device 10 the cartridge 12 is intended for. Hence, the data stored in the cartridge 12 may specify and determine, that only such drive mechanism 22 may be used featuring a piston rod having a diameter within a high pre-defined range and which matches with the present type of cartridge 12.

Additionally, the storage 31 of the cartridge 12 and the corresponding request 35 generated by the microprocessor 30 may be instructive about the various steps of assembly, the particular assembly stage 34 or subsequent assembly stages 36 have to execute.

Upon receipt of the request 35, the assembly stage 34 executes a corresponding assembly step and may confirm execution of said step by transmitting a respective response 33 to the cartridge 12. The response 33 may be indicative of physical, chemical and/or environmental parameters applied during the assembly step executed by the assembly stage 34. The response 33 and the data transmitted therewith is appropriately processed by the microprocessor 30 and is stored in the storage 31 of the cartridge, which is preferably of non-volatile type.

For instance, the response 33 may be indicative of assembly parameters, such like magnitude of mechanical pressure exerted and/or geometric displacement of various device components during the assembly process. Moreover, the response 33 may be indicative of environmental conditions. Hence, temperature, pH-value as well as humidity or other environment-specific parameters which could have an influence on the device 10 and the medicament contained in the cartridge 12 can be appropriately stored. This way, a medicament and device history can be generated and permanently stored in the storage 31 of the cartridge 12.

The response 33 may also confirm the request 35 of the cartridge 12 and may indicate to the cartridge 12, that the requested step of manufacture or assembly has now been completed. By way of the assembly step executed by the assembly stage 34 the cartridge 12 may have been disposed inside a cartridge holder 14, thereby forming a respective pre-assembly of the drug delivery device 10. When the cartridge 12 receives the confirmation 35 of the assembly stage 34, the cartridge 12 itself may induce or trigger a transport process to become transported in direct vicinity of another, subsequent assembly stage 36. Once arrived at the subsequent assembly stage 36, the cartridge 12, hence the preassembly of cartridge 12 and cartridge holder 14 may send another request 35 to trigger a subsequent step of assembly or manufacture.

As further illustrated in FIG. 2, the assembly stages 34, 36 may be equipped with stacks 40, 50 of various device components 42, 44, 46, which may be selected and taken during respective steps of assembly in order to be assembled with the available pre-assembly.

Considering for instance the step of assembling cartridge 12 and cartridge holder 14, the stack 40 of the assembly stage 34 may comprise differently sized or differently configured cartridge holders 42, 44, 46 appropriately sorted and categorized. For instance, the cartridge holder 42 is particularly configured for a first type of needle hub whereas a cartridge holder 44 may be configured to mate with a different kind of needle hub. Depending on the overall device specification provided and stored in the storage 31 of the cartridge 12, the assembly stage 34 may autonomously select the correct and appropriate cartridge holder 14 according to the request 35 send by the cartridge 12.

In response to the executed step of assembly, the storage 31 of the cartridge 12 may be provided with respective information, e.g. that a cartridge holder 14 of type 42 has been assembled with the cartridge 12. In a subsequent step of assembly to be conducted by another assembly stage 36, this but also other information stored in the storage 31 of the cartridge 12 can be used to select at least one of the items 52, 54, 56 in order to conduct the next assembly step. For instance, assembly of cartridge holder 42 requires to select a particular piston rod 52 among a variety of piston rods 52, 54, 56.

Furthermore, as indicated in FIG. 3, the assembly line 38 at least terminates with a release stage 60, where a final quality control of the drug delivery device 10 can be conducted. The final release check may comprise to read-out all or at least some assembly-specific data from the storage 31 in order to process said data and to determine, whether the device 10 has been correctly assembled. In case that an inappropriate assembly is determined by the release stage 60, the corresponding device 10 is taken away from the assembly or manufacturing process; hence it is sorted out.

Additionally or alternatively it is conceivable, that a processing of data regarding type and/or geometry of mutually assembled components is conducted on-site by the microprocessor 30 of the cartridge 12 itself. Instead of getting sorted out in a passive way, the cartridge 12 may actively transmit a request of rejection to the release stage 60 in response of which the respective pre-assembly or the entire drug delivery device 10 is sorted out and taken away. By implementing such release stages 60 not only at the end of the assembly line 38 but also between various selected assembly stages 34, 36, an inappropriate assembly or pre-assembly can be detected at a very early stage, eventually in such a way, that at least some components thereof can be disassembled and re-used again. This way, the amount of defected goods and drug delivery devices can be effectively reduced.

Figure 4:
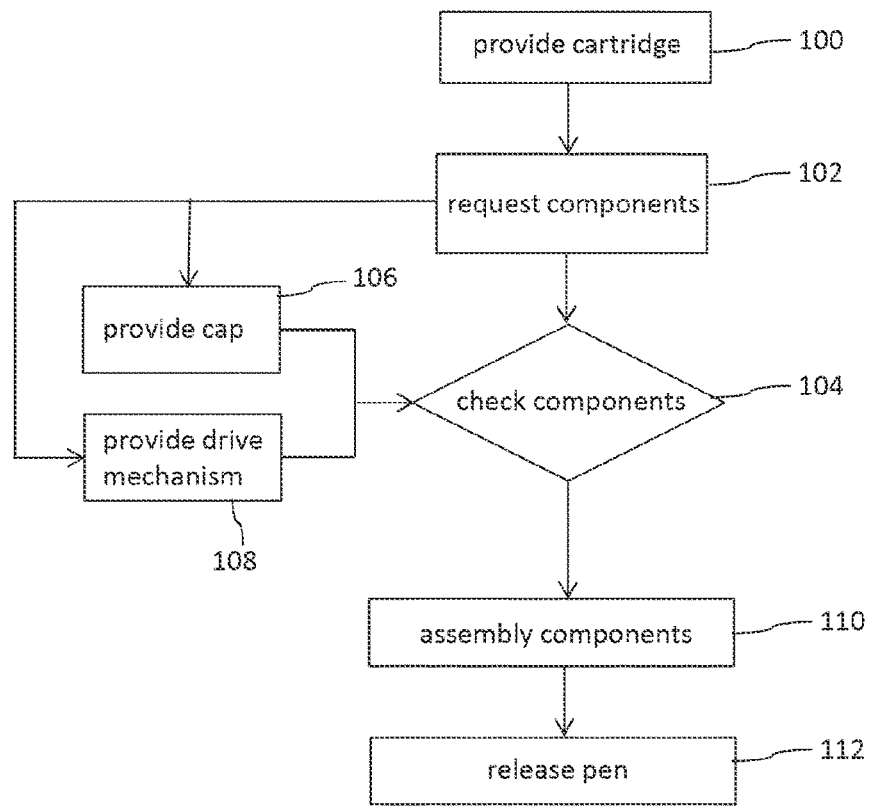
FIG. 4 shows a flowchart of a method to assemble various device components.

The illustrated scheme of e.g. a cartridge-controlled manufacture or assembly of a drug delivery device is universally applicable not only for the assembly of device components but also in the course of packaging of a device. FIG. 4 is illustrative of a flowchart of manufacturing and/or assembling a drug delivery device, such like a pen-type injector 10.

There, in an initial step 100, the cartridge 12 is provided and requests and initiates an assembly process 102. In response of the request 102, the assembly line 38 prepares requested components. Elsewhere in the assembly line 38, a requested cap 18 can be provided in step 106. Additionally, in step 108, an appropriate and requested drive mechanism can be provided. In a subsequent step 104, the components provided by steps 106, 108 are checked if they match with the components previously requested in step 102. If the provided combination of components matches with the requested components, the procedure continuous with step 110, wherein the requested components are mechanically interconnected and engaged. At the end, in step 112, the drug delivery device 10 is completed. Upon completion and/or during or between single steps of device assembly, device- and/or production- or assembly-specific data is stored in the storage of the drug delivery device 10, e.g. in step 112.

Figure 5:
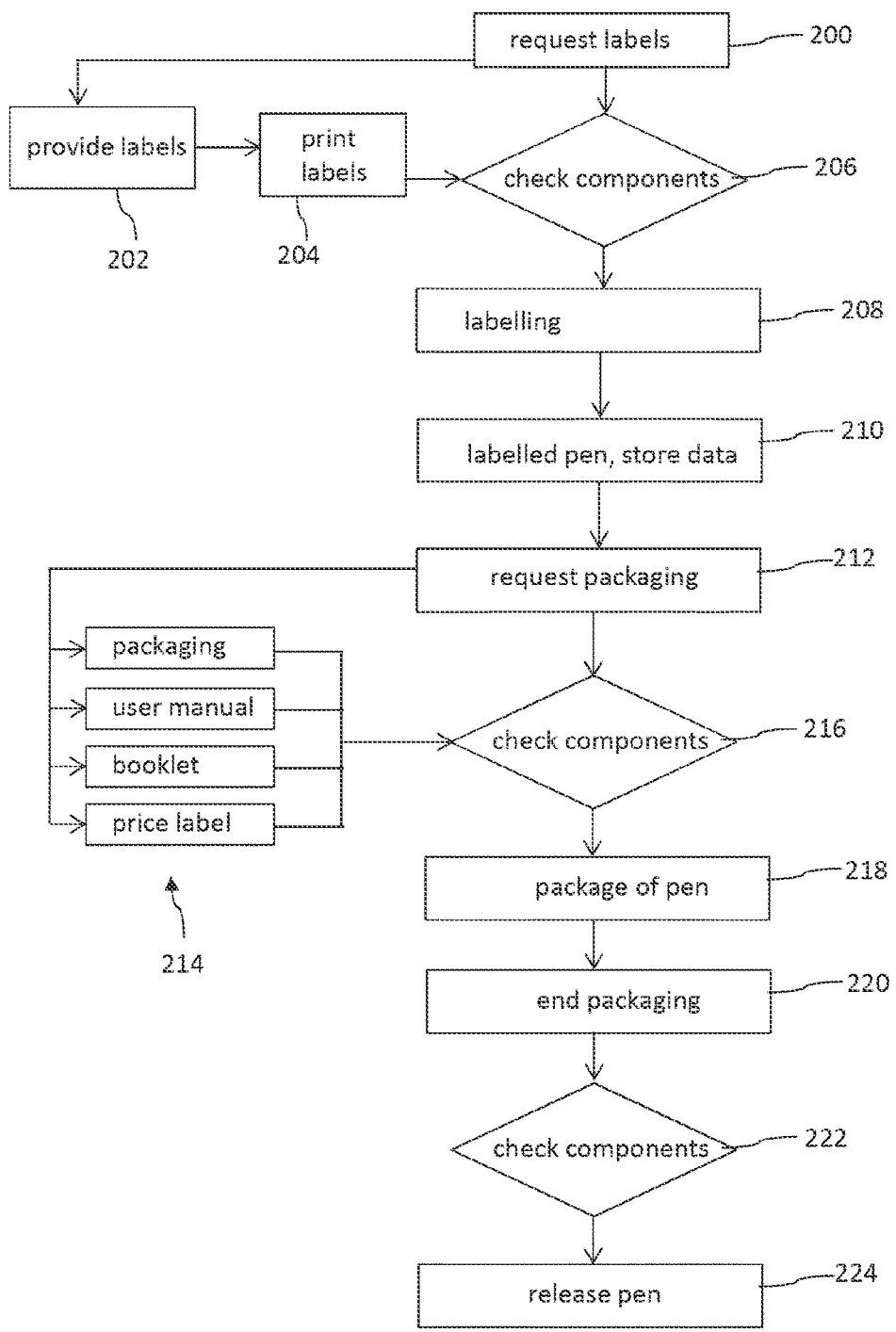
FIG. 5 is illustrative of a flowchart of a method to be conducted by the assembly line during packaging of the device in a secondary packaging.

A similar method as illustrated by the flowchart as shown in FIG. 5 may directly follow the assembly process according to FIG. 4. Once the device 10 is finally assembled in step 110 of FIG. 4, in a subsequent step 200 of FIG. 5, respective labels to be combined with the device 10 are requested. Labels according to the particular type of cartridge may be requested via data stored in and provided by the cartridge in step 202. The at least one or various labels may be printed according to the device-specific information in step 204. Prior to attach the at least one label to the device in step 208, in step 206 it is first checked, whether the labels prepared in steps 202 and 204 correctly match with the labels as requested in step 200. Prior, during or after labelling the pen-type injector in step 208, respective labelling information is stored in the storage 31 of the cartridge 12 in step 210. With step 210, labelling of the drug delivery device 10 is substantially completed.

Thereafter, in step 212 a secondary packaging is requested, which in a similar way has already been appropriately configured in step 214. In step 214, an appropriate packaging, leaflets and booklets as well as user guides and price information are provided on request of the device 10. Secondary packaging, user information, booklets, leaflets and price information are configured according to the market, be device is to be distributed and/or according to the properties of the device and the medicament provided therein. Providing and preparing of the packaging and information material is conducted in accordance with the data previously received from the storage 31 of the cartridge.

In step 216, the items provided in step 214 are checked and compared with the items requested in step 212. Thereafter, in step 218, the device is disposed in the secondary packaging, e.g. together with e.g. language-specific leaflets or booklets. Moreover, the secondary packaging may be imprinted with device-, language- or market-specific data. In a subsequent step 220, the packed device may be palletized and/or finally packaged.

In a last and subsequent check 222, it is checked, whether the device is configured in a plausible way. This final check 222 may be conducted on the basis of processing and/or evaluating the data contained in the storage 31 of the device and/or of its cartridge 12. If this final quality check 222 is passed, the device will be finally released to the market.

The invention claimed is:

1. A cartridge for an injection device the cartridge being configured for mechanical assembly with at least one further component of the injection device to form a pre-assembly of the injection device, wherein the cartridge comprises:
   a container being at least partially filled with a liquid medicament to be dispensed by the injection device,
   a piston slidably disposed in the container and sealing the container,
   a microprocessor,
   a writable storage to store assembly related data including an assembly configuration of the injection device,
   a communication member in electrical contact with the microprocessor and the writable storage, wherein at least one of the microprocessor, the writable storage and the communication member is embedded in or disposed on the piston, and
   instructions stored in the writable storage and executable by the microprocessor to carry out functions comprising:
   providing assembly related data from the communication member to an automated assembly line adapted to assemble the injection device, and
   providing steps of assembly from the communication member to the automated assembly line according to the assembly related data stored by the writable storage.

2. The cartridge component according to claim 1, wherein the cartridge is an initial component of the injection device, and wherein the microprocessor is further operable to select and/or to determine the type and/or configuration of subsequent device components of the injection device to be assembled.

3. The cartridge according to claim 1, wherein the microprocessor is adapted to process assembly-related and/or to process injection device-related data.

4. The cartridge according to claim 3, wherein the microprocessor is adapted to validate and/or to approve if the pre-assembly fulfills pre-defined conditions of release.

5. The cartridge according to claim 4, wherein the microprocessor in response of not meeting the conditions of release is operable to request ejection of the pre-assembly from the assembly line.

6. An assembly line to assemble an injection device and comprising at least one communication member adapted to communicate with a corresponding communication member of a cartridge of the injection device according to claim 1 as an initial device component, and further comprising:
   at least one assembly stage adapted to conduct at least one step of assembly being at least influenced by injection device-related data obtained from the initial device component.

7. The assembly line according to claim 6, wherein the assembly stage is adapted to select at least a further device component of the injection device as a selected device component among a plurality of device components and is further adapted to assemble the selected device component with the initial device component on request of the initial device component's microprocessor.

8. The assembly line according to claim 6, wherein the at least one assembly stage is adapted to store assembly-related data in the storage of the initial device component.

9. The assembly line according to claim 6 further comprising a release stage to read-out the storage of the initial device component and to determine whether pre-defined conditions of release are met.

10. A method of assembling an injection device comprising the steps of:
   providing a cartridge according to claim 1 as an initial device component,
   receiving device-related data from the initial device component,
   selecting at least one device component as a selected device component according to the received data,
   assembling the selected device component with the initial device component thereby forming a pre-assembly,
   storing assembly-related data in the storage of the initial device component, and
   passing over the pre-assembly to a proceeding assembly stage.

11. The method according to claim 10, further comprising:
   at least partially storing an assembly configuration of the injection device in the storage of the initial device component, automatically conducting or instructing subsequent assembly stages of an automated assembly line regarding preceding steps of assembly and/or regarding pre-defined data.

12. A cartridge for assembly into a drug delivery device, the cartridge comprising:
   a tubular shaped body at least partially filled with a medicament and sealed by a piston displaceable along a longitudinal direction of the tubular body, the piston comprising:
   a microprocessor,
   a writable storage to store assembly-related data, and instructions executable by the microprocessor,
   and a communication member to provide device-related data to an automated assembly line, the assembly line being configured to assemble the drug delivery device;
   wherein at least one of the microprocessor, the writable storage and the communication member is embedded or disposed in the piston;
   wherein the stored assembly-related data includes assembly configuration of the drug delivery device;
   where instructions on the writable storage are executable by the microprocessor to:
   provide assembly-related data from the communication member to an automated assembly line adapted to assemble the drug delivery device; and
   provide steps of assembly from the communication member to the automated assembly line according to the assembly-related stored data.

* * * * *